United States Patent
Ishibashi et al.

(10) Patent No.: US 9,643,958 B2
(45) Date of Patent: May 9, 2017

(54) DEPROTECTION METHOD FOR PROTECTED HYDROXYL GROUP

(71) Applicant: Asahi Glass Company, Limited, Chiyoda-ku (JP)

(72) Inventors: Yuichiro Ishibashi, Chiyoda-ku (JP); Yasushi Matsumura, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 161 days.

(21) Appl. No.: 14/057,384

(22) Filed: Oct. 18, 2013

(65) Prior Publication Data

US 2014/0058113 A1   Feb. 27, 2014

Related U.S. Application Data

(63) Continuation of application No. PCT/JP2012/060623, filed on Apr. 19, 2012.

(30) Foreign Application Priority Data

Apr. 21, 2011  (JP) ................................. 2011-095211

(51) Int. Cl.
*C07D 405/06* (2006.01)
*C07B 51/00* (2006.01)
*C07C 29/10* (2006.01)

(52) U.S. Cl.
CPC ............ *C07D 405/06* (2013.01); *C07B 51/00* (2013.01); *C07C 29/10* (2013.01)

(58) Field of Classification Search
None
See application file for complete search history.

(56) References Cited

U.S. PATENT DOCUMENTS

2008/0280859 A1   11/2008   Adorini et al.

FOREIGN PATENT DOCUMENTS

| JP | 62-120325 | 6/1987 |
|----|-----------|--------|
| JP | 6-211703  | 8/1994 |
| JP | 6-234675  | 8/1994 |
| JP | 8-27152   | 1/1996 |

OTHER PUBLICATIONS

Chu et al., J. Org. Chem., 2003, No. 68, pp. 55-61.*
Prostaglandin. (n.d.) The American Heritage® Medical Dictionary. (2007). Retrieved May 4, 2015 from http://medical-dictionary.thefreedictionary.com/prostaglandin.*
Corey et al., J. Am. Chem. Soc., 1988, 110, pp. 3673-3674.*
Griffon et al., Collect. Czech. Chem. Commun., 2006, vol. 71, No. 7, pp. 1063-1087.*
International Search Report issued Jul. 12, 2012 in PCT/JP2012/060623 filed Apr. 19, 2012.
P. Arumugam, et al., "A Mild, Efficient, and Inexpensive Protocol for the Selective Deprotection of TBDMS Ethers Using $KHSO_4$", Chemistry Letters, 2004, vol. 33, No. 9, pp. 1146-1147.
B. Das, et al., "A simple, efficient and highly selective deprotection of t-butyldimethylsilyl (TBDMS) ethers using silica supported sodium hydrogen sulfate as a heterogeneous catalyst", Tetrahedron Letters, 2006, vol. 47, No. 33, pp. 5855-5857.
Takashi Yanagi, et al., "The Practical Synthesis of a Uterine Relaxant, Bis(2-{[(2S)-2-({(2R)-2-hydroxy-2-[4-hydroxy-3-(2-hydroxyethyl)-phenyl]ethyl}amino)-1,2,3,4-tetrahydronaphthalen-7-yl]oxy}-N,N-dimethylacetamide) Sulfate (KUR-1246)", Chemical & Pharmaceutical Bulletin, 2001, vol. 49, No. 8, pp. 1018-1023.
A. I. Meyers, et al., "Asymmetric Tandem Addition to Chiral 1- and 2-Substituted Naphthalenes. Application to the Synthesis of (=)-Phyltetralin", Journal of the American Chemical Society, 1988, vol. 110, No. 14, pp. 4611-4624.
Barry Lygo, et al., "Reaction of Dianions Derived from β-Ketoesters with Epoxides: Utility in the Preparation of Synthetically Useful Tetrahydrofurans.", Tetrahedron, 1988, vol. 44, No. 22, pp. 6881-6888.
Yosuke Kaburagi, et al., "Operationally Simple and Efficient Workup Procedure for TBAF-Mediated Desilylation: Application to Halichondrin Synthesis", Organic Letters, 2007, vol. 9, No. 4, pp. 723-726.
Andrew S. Kende, et al., "Total Synthesis of the Macrolide Antitumor Antibiotic Lankacidin C", J. Am. Chem. Soc. 1995, 117, pp. 8258-8270.
Guncheol Kim, et al., "The Total Synthesis of Indolizomycin", J. Am. Chem. Soc. 1993,115, pp. 30-39.
Carl E. Crouthamel, et al., "Spectrophotometric Studies of Dilute Aqueous Periodate Solutions", J. Am. Chem. Soc. 1949, vol. 71, pp. 3031-3035.
C. E. Crouthamel, et al., "Ionization and Hydration Equilibria of Periodic Acid", J. Am. Chem. Soc. 1951, vol. 73, pp. 82-87.
Greene, T.W. and Wuts, P.G.M. (1999) Protection for the Hydroxyl Group, Including 1,2- and 1,3-Diols, in Protective Groups in Organic Synthesis, Third Edition, John Wiley & Sons, Inc., New York, USA. doi: 10.1002/0471220574.ch2.
World Encyclopedia (Heibonsha Limited, Publishers), $2^{nd}$ ed., section for periodic acid , pp. 112-113 (2006).

* cited by examiner

*Primary Examiner* — Alicia L Otton
(74) *Attorney, Agent, or Firm* — Oblon, McClelland, Maier & Neustadt, L.L.P.

(57) ABSTRACT

To deprotect an alcoholic hydroxyl group protected by a t-butyldimethylsilyl group without influencing a functional group unstable to an acid. In the presence of a solvent, an alcohol having a hydroxyl group protected by a t-butyldimethylsilyl group is deprotected in the presence of an acid or an acid salt having a pKa of from 1.0 to 3.0 in water.

11 Claims, No Drawings

DEPROTECTION METHOD FOR PROTECTED HYDROXYL GROUP

TECHNICAL FIELD

The present invention relates to a method for efficiently deprotecting an alcohol compound protected by a t-butyldimethylsilyl group.

BACKGROUND ART

Heretofore, in carrying out various organic synthetic reactions, it has been common to protect an alcoholic hydroxyl group in a raw material compound in an inactive form. Usually, such "protection" is carried out by directly bonding a compound so-called a protective group to an alcoholic hydroxyl group to be inactivated. After completion of the necessary reaction, the compound bonded to the hydroxyl group is disconnected, whereby the protected hydroxyl group is freed to be in an initial state. This operation is "deprotection".

A t-butyldimethylsilyl group (TBS group) is known as a protective group which makes protection and deprotection possible under a relatively mild condition.

Known as a method for protection by a TBS group is, for example, a method of reacting t-butyldimethylchlorosilane and imidazole to an alcohol at room temperature in a dimethylformamide solvent, or a method of reacting t-butyldimethylchlorosilane and lithium sulfide to an alcohol at room temperature in an acetonitrile solvent, whereby the alcohol can be easily converted to a TBS ether under a mild condition. Here, the TBS ether is meant for the alcohol protected by a t-butyldimethylsilyl group (TBS group).

The TBS ether is stable under a basic condition and inert to a reaction with e.g. an alcoholate or enolate, a nucleophile such as lithium aluminum hydride, an organic metal compound such as n-butyl lithium, a Grignard reagent or lithium hexamethyldisilazide, or an oxidizing agent such as chromic acid, and therefore, it is widely used as a protective group for an alcohol in a reaction such as an aldol reaction, a Wittig reaction or a Swern oxidation. Particularly, it is very useful as a protective group for compounds which are unstable to an acid, among natural products, their derivatives, intermediates, etc. Such natural products include, for example, antibiotic substances such as β-lactam, macrolide, etc., lipid-related substances such as prostaglandin, leukotriene, etc., nucleic acid and sugars, anticancer drugs such as taxanes, furaquinocins, etc., ginkgolide, palytoxin, etc., and they are used, for example, in their derivatives or intermediates in many cases.

Deprotection methods for a TBS group are summarized in Non-patent Document 1. Common deprotection methods for a TBS group are broadly classified into a method by means of fluoride ions and a method by means of an acid (such as a Bronsted acid or a Lewis acid). As other methods, examples are reported wherein N-bromosuccinimide, diisobutyl aluminum hydride or a palladium complex is employed, but none of them is a method having substrate generality.

The deprotection method by means of fluoride ions may, for example, be a method of employing hydrofluoric acid, a method of employing an amine complex of hydrogen fluoride, such as pyridine-nHF or triethylamine-nHF, a method of employing an inorganic salt such as cesium fluoride, potassium fluoride, lithium borofluoride ($LiBF_4$) or ammonium fluoride, or a method of employing an organic salt such as tetrabutylammonium fluoride (TBAF). However, hydrofluoric acid is highly toxic and is therefore not easy to handle. The amine complex of hydrogen fluoride is better in safety than hydrofluoric acid, but it still has a possible danger of releasing hydrofluoric acid and is lower than hydrofluoric acid in the ability as a deprotecting agent, and its price is also high. The inorganic fluoride salt has a low solubility in an organic solvent which is usually used in the deprotection, and its ability as a deprotecting agent is also not sufficient.

Tetrabutylammonium fluoride (TBAF) is superior to other deprotecting agents having fluoride ions in the safety, the solubility in an organic solvent and the ability as a deprotecting agent, and it is therefore frequently used in deprotection to remove a TBS group.

However, if TBAF is employed, a large amount of an ammonium salt will remain after the reaction, and for its removal, it is necessary to add water and carry out extraction and washing. This operation becomes to be a very cumbersome step particularly when the production is in a large scale and thus, is not suitable for the production in a large scale.

In order to avoid such an extraction and washing step after the deprotection, in Non-patent Document 2, the ammonium salt is removed by adding an ion exchange resin and calcium carbonate to the reaction solution after deprotecting the alcoholic hydroxyl group by means of TBAF, to have TBAF and other ammonium salts ion-bonded to the ion exchange resin, followed by filtration. However, this method requires filtration instead of the extraction and washing step.

Further, TBAF is a basic compound and its fluoride ions have nucleophilicity, whereby it has a drawback such that it cannot be used for a compound which is weak under a basic condition or a compound which is reactive with a nucleophile. Further, TBAF has such a nature that it is difficult to deprotect a TBS ether which is sterically crowded, whereby it frequently requires a high temperature and a long time for deprotection of a TBS ether of e.g. a secondary alcohol.

On the other hand, in the deprotection by means of a Bronsted acid or a Lewis acid, it is considered that an oxygen atom of an alcohol protected by TBS will be coordinated to the proton or Lewis acid, and the TBS group will be removed. Accordingly, the deprotection speed depends largely on the strength and concentration of the acid to be used. Principal protonic acids to be used for deprotection to remove a TBS group as disclosed in Non-patent Document 1 are as follows. Here, a numeral in brackets represents pKa (in water) as an index showing the strength of the acid, and the smaller the numeral, the stronger the acid. In the case of a so-called polybasic acid having a plurality of ionizable active hydrogen, pKa based on the first stage acid dissociation constant (Ka) is disclosed. Trifluoromethanesulfonic acid (−14), hydrochloric acid (−8), sulfuric acid (−3), methanesulfonic acid (−3), p-toluenesulfonic acid (−1), an ion exchange resin having a p-toluenesulfonic acid group at its terminal, trifluoroacetic acid (0.2), periodic acid (1.6), hydrofluoric acid (3.2), formic acid (3.8), acetic acid (4.8). According to Non-patent Document 1, an alcohol protected by a TBS group is deprotected (high reactivity) in an aqueous solution having a pH of at most 4, but is not deprotected (low reactivity) in an aqueous solution having a pH of more than 4. Deprotection to remove a TBS group will be easy by using a strong acid such as trifluoromethanesulfonic acid, but in the case of deprotection of a compound containing a moiety weak to an acid, decomposition is likely to occur during the deprotection. On the other hand, if a weak acid such as acetic acid or formic acid is used, deprotection to remove a TBS group may not proceed smoothly. In order to accelerate the reaction, a method of heating or increasing the concentration is available, but in such a case, a compound containing a moiety weak to an acid may sometimes be decomposed. Further, acetic acid or formic acid has a high solubility in an organic solvent and also has a high boiling point, and therefore, in a case where it is not possible to use an alkaline aqueous solution for extraction and washing after the reaction, e.g. in a case where the objective alcohol is unstable under an alkaline condition or in a case the objective compound itself is also an acid, it has a drawback such that removal of acetic acid or formic acid tends to be difficult by either method of extraction and washing or distillation under reduced pressure.

In Non-patent Document 3, formic acid is used for deprotection to remove a TBS group in a total synthesis of natural product (−)-Lankacidin C. In this case, formic acid is reacted with a TBS-protected product of allyl alcohol being an intermediate unstable to fluoride ions or hydrogen fluoride, at room temperature for 3 hours in a mixed solvent of tetrahydrofuran (THF) and water, to obtain the deprotected alcohol in a yield of 82%. However, as mentioned above, formic acid has a high solubility in an organic solvent and also has a high boiling point, and it is often difficult to remove it.

In Non-patent Document 4, periodic acid is used for deprotection of a TBS group in a total synthesis of Indolizomycin. In this case, an aqueous periodic acid solution is added to a TBS-protected product of a secondary alcohol dissolved in tetrahydrofuran (THF) and reacted therewith at room temperature for 8 hours to obtain the deprotected alcohol. However, periodic acid has an explosive nature, and in order to use it in an industrial scale, it is required to install an explosion-proof equipment. It is noted that there is a literature in which the pKa value of periodic acid in water is disclosed to be 1.6 (Non-patent Document 5), but in a subsequent literature, it has been corrected to be 3.3 (Non-patent Document 6), and in a recent book, a value of 3.3 has been adopted as the pKa (Non-patent Document 7).

In Patent Document 1, deprotection of an alcohol protected by a trimethylsilyl group which can be removed more easily than a TBS group, is carried out by means of oxalic acid which is an acid stronger than formic acid. In this document, the deprotection is carried out by reacting a compound having a plurality of hydroxyl groups protected by a TBS group and a trimethylsilyl group in the same compound, with oxalic acid in methanol at room temperature, whereby, while the trimethylsilyl group is easily removed, the TBS group is not removed. The TBS group is removed by means of TBAF or an aqueous solution of fluorosilicic acid ($H_2SiF_6$) which is an acid stronger than oxalic acid, and it is understood that a TBS group will not be removed by oxalic acid depending upon the solvent and temperature conditions.

PRIOR ART DOCUMENTS

Patent Document

Patent Document 1: US2008/0280859 A1

Non-Patent Documents

Non-patent Document 1: "PROTECTIVE GROUPS in ORGANIC SYNTHESIS (3rd ed.)"
Non-patent Document 2: Org. Let. 2007, Vol. 9, p 723
Non-patent Document 3: J. Am. Chem. Soc. 1995, Vol. 117, p 8258
Non-patent Document 4: J. Am. Chem. Soc. 1993, Vol. 115, p 30
Non-patent Document 5: J. Am. Chem. Soc. 1949, Vol. 71, p 3031
Non-patent Document 6: J. Am. Chem. Soc. 1951, Vol. 73, p 82
Non-patent Document 7: World Encyclopedia (Heibonsha Limited, Publishers), 2nd ed., section for periodic acid

DISCLOSURE OF INVENTION

Technical Problem

It is an object of the present invention to develop a novel deprotection method for an alcohol hydroxyl group thereby to make efficient deprotection possible for an alcohol having an unstable moiety to an acid, which used to be difficult to attain.

Solution to Problem

The present inventors have conducted a research in order to accomplish the above object and have found it possible to carry out deprotection without decomposition even for an alcohol having a moiety weak to an acid by the following method wherein the type of an acid and the solvent are suitably selected. Thus, the present invention provides the following.

(1) A deprotection method which comprises subjecting an alcohol having a hydroxyl group protected by a t-butyldimethylsilyl group to remove the t-butyldimethylsilyl group, wherein the deprotection is carried out in the presence of an acid or an acid salt having a pKa of from 1.0 to 3.0 in water.
(2) The method according to (1), wherein the pKa of the acid or the acid salt in water is from 1.0 to 2.0.
(3) The method according to (1) or (2), wherein the acid is a carboxylic acid.
(4) The method according to (3), wherein the carboxylic acid has at least two carboxyl groups per molecule.
(5) The method according to (3) or (4), wherein the carboxylic acid is oxalic acid or maleic acid.
(6) The method according to (1) or (2), wherein the acid salt is an acidic inorganic acid salt.
(7) The method according to (6), wherein the acidic inorganic acid salt is a hydrogen sulfate of an alkali metal or ammonium.
(8) The method according to (7), wherein the acidic inorganic acid salt is sodium hydrogen sulfate.
(9) The method according to any one of (1) to (8), wherein as the solvent, a mixed solvent of an organic solvent and water, is used.
(10) The method according to (9), wherein the proportion of water in the mixed solvent is 0.01≤water/(organic solvent+water)≤0.8 by volume ratio.
(11) The method according to any one of (1) to (8), wherein the reaction temperature is from 0 to 100° C.
(12) The method according to any one of (1) to (11), wherein the deprotected alcohol is an alcohol having at least one moiety unstable to an acid, selected from a vinyl ether moiety, an allyl ether moiety, an allyl alcohol moiety, an acetal moiety, a β-hydroxycarbonyl moiety, a tetrahydropyranyloxy group, an epoxy group, an amide bond, an ester bond and a polyene moiety.
(13) The method according to any one of (1) to (12), wherein the deprotected alcohol is a prostaglandin having a moiety unstable to an acid.

Advantageous Effects of Invention

According to the present invention, an alcohol protected by TBS can efficiently be deprotected under a mild condition. Further, according to the present invention, deprotection can be made stably even for an alcohol having a moiety unstable to an acid.

DESCRIPTION OF EMBODIMENTS

Now, the present invention will be described in detail.
[Alcohol]

The alcohol to be used in the present invention is not particularly limited, and for example, it may be either an aliphatic alcohol such as 1-octanol or 2-octanol, or an aromatic alcohol such as phenol or cresol. The present invention is characterized in that it is capable of deprotecting an alcohol protected by TBS without damaging a moiety unstable to an acid, and accordingly, the deprotection method of the present invention is applicable particularly effectively to an alcohol having a moiety unstable to an acid. The moiety unstable to an acid may, for example, be a vinyl ether moiety (a), an allyl ether moiety (b), an allyl alcohol moiety (c), an acetal moiety (d), a β-hydroxycarbonyl moiety (e), a tetrahydropyranyloxy group (f), an epoxy group (g), an amide bond (h), an ester bond (i) or a polyene moiety (j).

The skeletal structures of the respective moieties are shown below.

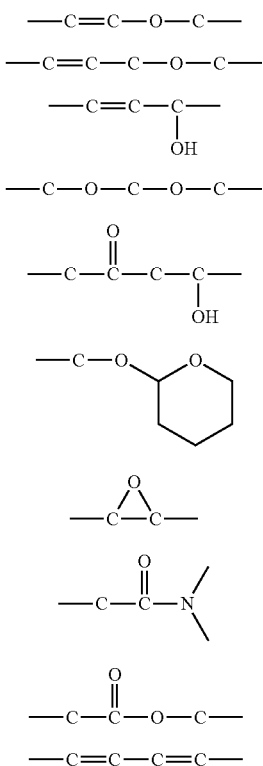

To carbon and nitrogen atoms in the above skeletal structures, a carbon atom, a hydrogen atom, a halogen atom (a fluorine atom, a chlorine atom, a bromine atom or an iodine atom), a nitrogen atom, an oxygen atom, a silicon atom, a phosphorus atom, a sulfur atom, etc. are bonded. A compound having the above allyl alcohol moiety (c) or β-hydroxycarbonyl moiety (e) may further have a hydroxyl group. Further, the alcohol may have two or more of these skeletal structures.

Among alcohols having the above skeletal structures, compounds having a vinyl ether moiety (a), an allyl ether moiety (b), an allyl alcohol moiety (c), a β-hydroxycarbonyl moiety (e) or an epoxy group (g) are particularly preferred, since these moieties are particularly unstable to an acid, and compounds having a vinyl ether moiety (a), an allyl alcohol moiety (c) or a β-hydroxycarbonyl moiety (e) are most preferred.

As the alcohol to be used in the present invention, a prostaglandin is particularly preferred. In the present invention, the prostaglandin includes various natural prostaglandins and their derivatives, which are compounds having at least one hydroxyl group. Many of such prostaglandins have at least one type of the above-mentioned moieties unstable to an acid, together with the hydroxyl group. Particularly, they have a vinyl ether moiety (a), an allyl alcohol moiety (c) or both of them. Therefore, in the syntheses of such prostaglandins wherein various chemical conversions are carried out while protecting their hydroxyl groups, followed by deprotection to obtain prostaglandins having freed hydroxyl groups, it is preferred to carry out the deprotection by the deprotection method of the present invention.
[Acid and Acid Salt]

In the present invention, as an acid substance for deprotection, an acid or an acid salt having a pKa of from 1.0 to 3.0 in water is used. The acid may be an organic acid or an inorganic acid. The acid salt may also be an acid salt of an organic acid or an acid salt of an inorganic acid.

Of the acid or the acid salt, if the pKa is larger than 3.0, the deprotection reaction to remove a TBS group tends to be slow, such being not practical. On the other hand, if the pKa is smaller than 1.0, the possibility of damaging the compound unstable to an acid tends to increase.

Preferably, a carboxylic acid having a pKa of from 1.0 to 3.0 in water, or an acidic inorganic acid salt having a pKa of from 1.0 to 3.0, is used. As other acid substances, inorganic acids such as sulfurous acid having a pKa of 1.9 in water, and phosphoric acid having a pKa of 2.1 in water, may be mentioned.
[Carboxylic Acid]

The carboxylic acid to be used for deprotection of the present invention may be a carboxylic acid having one carboxyl group per molecule (monobasic carboxylic acid) or a carboxylic acid having two or more carboxyl groups per molecule (polybasic carboxylic acid). Further, it may be a saturated carboxylic acid or an unsaturated carboxylic acid, and it may have a reactive group other than a carboxyl group, a halogen atom, etc. The carboxylic acid having a pKa of from 1.0 to 3.0 in water may, for example, be an aliphatic carboxylic acid such as oxalic acid (pKa: 1.2), dichloroacetic acid (pKa: 1.3), maleic acid (pKa: 1.9), monochloroacetic acid (pKa: 2.9), monobromoacetic acid (pKa: 2.9), fumaric acid (pKa: 3.0) or malonic acid (pKa: 2.8), an aromatic carboxylic acid such as nitrobenzoic acid (pKa: 2.2) or phthalic acid (pKa: 3; 0), or an amino acid such as alanine (pKa: 2.4), glycine (pKa: 2.3) or cysteine (pKa: 1.7). Among them, a carboxylic acid having no amino group is preferred from the viewpoint of the solubility in a solvent.
[Acidic Inorganic Acid Salt]

The acidic inorganic acid salt having a pKa of from 1.0 to 3.0 in water is an acid salt of an inorganic acid such as sulfuric acid, and the inorganic acid is preferably an inorganic acid containing no halogen. The acidic inorganic acid salt is particularly preferably a hydrogen sulfate. The hydrogen sulfate may, for example, be an alkali metal salt or an ammonium salt such as sodium hydrogen sulfate (pKa: 2.0), potassium hydrogen sulfate (pKa: 2.0) or ammonium hydrogen sulfate (pKa: 2.0). In a case where the acidic inorganic acid salt may take a form of an anhydride or a hydrate, either one may be employed. In a case where a hydrate is to be used, the amount of hydrated water contained in the acidic inorganic acid salt is calculated, and the amount of water to be used as a solvent is reduced in an amount corresponding to the hydrated water in the acidic inorganic acid salt, whereby it is possible to obtain the same results as in a case where an anhydride of the acidic inorganic acid salt is used.

Among the above acids and acid salts (both of them may hereinafter be referred to generally as the acids), those having a pKa of from 1.0 to 2.0 in water are particularly preferred in view of the reaction rate and presenting a less damage to a compound unstable to an acid. Such acids are capable of carrying out the deprotection without damaging an alcohol protected by TBS by using the after-described solvent and adjusting the reaction temperature and time.

Further, depending upon the structure of an alcohol as the objective compound, there is a case where it is not possible to carry out extraction and washing with an alkaline aqueous solution, and therefore, the acid is preferably one which can easily be removed by extraction and washing with neutral water. Such an acid may, for example, be a dibasic carboxylic acid such as oxalic acid, maleic acid, fumaric acid or malonic acid, or a hydrogen sulfate such as sodium hydrogen sulfate, potassium hydrogen sulfate or ammonium hydrogen sulfate.

Oxalic acid, maleic acid, sodium hydrogen sulfate, potassium hydrogen sulfate and ammonium hydrogen sulfate are most preferred, since they have a pKa of from 1.0 to 2.0, are excellent in removability at the time of extraction, can be easily handled as a solid stable at room temperature and are less toxic to a human body or environment.

The acid in the present invention serves as a catalyst for deprotection, and from the viewpoint of the reaction formula, there is no limit in the amount of the acid. Practically, as the amount of the acid added increases, the reaction tends to proceed smoothly, but the possibility of a side reaction tends to increase. Also from the viewpoint of the raw material cost, the smaller the amount of the acid to be added, the better. Thus, the amount of the acid to be added is preferably from 0.05 to 20, more preferably from 0.1 to 10, most preferably from 0.2 to 5, by the number of moles of active hydrogen/the number of moles of the alcohol protected by TBS. Here, active hydrogen is meant for hydrogen atoms which are ionized to become protons in the reaction solution, among hydrogen atoms contained in the acid.

[Solvent]

In the present invention, it is preferred to use a mixed solvent of an organic solvent and water. By adding water, the deprotection reaction will be accelerated, and it is possible to suppress a side reaction such as decomposition of the substrate. The mechanism whereby such effects are developed by the addition of water, is not clearly understood, but it is considered that an unstable intermediate is readily protonated and converted to a stable alcohol thereby to provide an effect to suppress a side reaction, and water coordinates to the acid to make the reactivity mild thereby to provide an effect to let the deprotection proceed efficiently under wide temperature and time conditions. In order to let the effects of addition of water be developed, an organic solvent capable of dissolving at least 1 vol % of water at room temperature, may be used. An organic solvent capable of dissolving at least 5 vol % of water is preferred, and an organic solvent capable of dissolving at least 20 vol % of water is most preferred.

The solvent capable of dissolving at least 1 vol % of water may, for example, be an alcohol such as methanol, ethanol or isopropanol, an amide such as N,N-dimethylformamide, N,N-dimethylacetamide, N-methylpyrrolidone or N,N-dimethylimidazoline, a ketone such as acetone or ethyl methyl ketone, an ester such as ethyl acetate, an ether such as tetrahydrofuran, or a nitrile such as acetonitrile or propionitrile. From the viewpoint of the reaction rate and the deprotection yield, N,N-dimethylformamide, N,N-dimethylacetamide, acetonitrile, tetrahydrofuran or acetone is preferred, and among them, acetonitrile or tetrahydrofuran is most preferred.

One of these organic solvents may be mixed with water, or a plurality of such organic solvents may be mixed with water. The ratio of water to the organic solvent is preferably from 0.01 to 0.8, more preferably from 0.05 to 0.6, most preferably from 0.1 to 0.4, by volume ratio of water/(organic solvent+water), in order to let the TBS-protected alcohol be dissolved to a certain level in the solvent, while letting the effects of addition of water develop. The reaction proceeds either in a homogeneous system wherein the organic solvent and water are completely compatibilized, or in a two-phase system wherein the organic solvent and a part of water are separated. In many cases, even if the reaction system is a two-phase system at the initiation of the reaction, along with the progress of the reaction, a deprotected alcohol and t-butyldimethylsilanol will increase and serve as a good solvent for the substrate, whereby the system becomes uniform. A system wherein the solution becomes uniform at the completion of the reaction, is preferred, since the reaction thereby proceeds more smoothly.

[Concentration]

The concentration of the solution should better be high from the viewpoint of costs, but if the concentration is too high, the possibility for an undesirable side reaction such as a reaction of the deprotected alcohol itself increases. Therefore, the concentration by weight of the solution is preferably from 1 to 20%, more preferably from 3 to 15%, more preferably from 5 to 10%. The order of addition of the TBS ether, the organic solvent, water and the acid, is not particularly limited. However, in order to avoid contact of the TBS ether and the acid at a high concentration, it is preferred to add the TBS-protected alcohol or the acid lastly.

[Reaction Atmosphere, Temperature and Pressure]

The reaction in the present invention efficiently proceeds in air or in an inert gas such as nitrogen or argon. It is preferred to carry out the reaction in air, whereby the operation can be made at a lower cost. The reaction temperature is not particularly limited so long as it is within a range where the solvent is not solidified or boiled. However, with a view to reducing the reaction time and minimizing a damage to the substrate, it is preferably from 0 to 100° C., more preferably from 0 to 70° C., most preferably from 10 to 60° C. The reaction pressure for this reaction is not particularly limited, so long as it is not such a low pressure that the solvent will vaporize, but ordinary pressure is preferred whereby there will be no restriction with respect to a reaction device.

[Post Treatment]

The product obtained by the deprotection method for an alcohol of the present invention can be isolated and purified by a method which is commonly used for isolation and purification of usual organic compounds. For example, the reaction mixture may be treated with an aqueous sodium chloride solution or water and extracted by an organic solvent such as diethyl ether, ethyl acetate, methylene chloride or chloroform. The extract solution is dried over anhydrous magnesium sulfate or anhydrous sodium sulfate and concentrated to obtain a crude product, which may be purified by distillation, chromatography or recrystallization, as the case requires.

EXAMPLES

Measuring methods adopted in the present invention are as follows. Gas chromatography; Agilent 6850 Series manufactured by Agilent Technologies. HPLC; Agilent 1200 Series manufactured by Agilent Technologies. NMR; JNM-AL300, manufactured by JEOL Ltd.

Example 1

To a suspension prepared by mixing 0.2 g (0.82 mmol) of t-butyldimethyl(octyloxy)silane as a compound having 1-octanol protected by TBS, 12 ml of acetonitrile and 4 ml of water, 0.66 g (5.7 mmol) of maleic acid was added, followed by stirring in air at room temperature. Two hours later, the liquid was found to be uniform, and after confirming disappearance of the raw materials by thin-layer chromatography, 10 ml of water was added, followed by extraction twice with 10 ml of chloroform. The organic phase was concentrated under reduced pressure to obtain 0.13 g of a liquid, which was analyzed by gas chromatography and HPLC, whereby the yield of 1-octanol was 98%, and no maleic acid was detected.

The structural characteristics of the 1-octanol were as follows:

$^1$H-NMR (CDCl$_3$): δ 0.88 (m, 3H), 1.29-1.55 (m, 12H), 2.40 (s, 1H), 3.60 (t, 2H)

Example 2

To a suspension prepared by mixing 0.2 g (0.82 mmol) of t-butyldimethyl(2-octan-2-yloxy)silane as a compound having 2-octanol protected by TBS, 12 ml of acetonitrile and 4 ml of water, 0.66 g (5.7 mmol) of maleic acid was added, followed by stirring in air at room temperature. Two hours later, the liquid was found to be uniform, and after confirming disappearance of the raw materials by thin-layer chromatography, 10 ml of water was added, followed by extraction twice with 10 ml of chloroform. The organic phase was concentrated under reduced pressure to obtain 0.12 g of a liquid, which was analyzed by gas chromatography and HPLC, whereby the yield of 2-octanol was 96%, and no maleic acid was detected.

The structural characteristics of the 2-octanol were as follows:

$^1$H-NMR (CDCl$_3$): δ 0.89 (m, 3H), 1.18-1.51 (m, 12H), 1.68 (s, 1H), 3.80 (m, 2H)

Example 3

Deprotection of the following compound 2 as a compound having the following compound 1 protected by TBS, was carried out.

To a suspension prepared by mixing 1.5 g (2.2 mmol) of 4-[(Z)-(1S,5R,6R,7R)-6-[(1E,3R,4R)-3-t-butyldimethylsiloxy-4-(m-tolyl)-1-pentenyl]-7-t-butyldimethylsiloxy-2-oxa-4,4-difluoro-bicyclo[3.3.0]octan-3-ylidene]-1-(tetrazol-5-yl)butane (compound 2), 22.5 ml of acetonitrile and 7.5 ml of water, 0.37 g (3.2 mmol) of maleic acid was added, followed by stirring in air at room temperature. 24 hours later, the liquid was found to be uniform, and after confirming disappearance of the raw materials by thin-layer chromatography, 30 ml of water was added, followed by extraction twice with 30 ml of chloroform. The organic phase was concentrated under reduced pressure to obtain 1.1 g of a solid, which was analyzed by NMR, gas chromatography and HPLC, whereby the yield of 4-[(Z)-(1S,5R,6R,7R)-6-[(1E,3R,4R)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane (compound 1) was 98%, and no maleic acid was detected.

The structural characteristics of the compound 1 were as follows:

$^1$H-NMR (CD$_3$OD): δ 1.30 (d, J=7.0 Hz, 3H), 1.69 (dddd, J=14.6, 7.6, 3.0, 2.6 Hz, 1H), 1.82-1.95 (m, 2H), 2.10-2.16 (m, 2H), 2.29 (s, 3H), 2.31-2.41 (m, 2H), 2.48-2.56 (m, 1H), 2.72 (q, J=7.0 Hz, 1H), 2.93 (t, J=7.6 Hz, 2H), 3.78 (q, J=7.6 Hz, 1H), 4.04-4.10 (m, 1H), 4.69 (dt, J=6.48, 2.96 Hz, 1H), 4.79 (dt, J=7.6, 5.0 Hz, 1H), 5.36-5.46 (m, 2H), 6.95-7.13 (m, 4H).

$^{19}$F-NMR (CD$_3$OD): −116.6 (d, J=250.5 Hz), −84.8 (ddd, J=251.9, 17.3, 14.4 Hz).

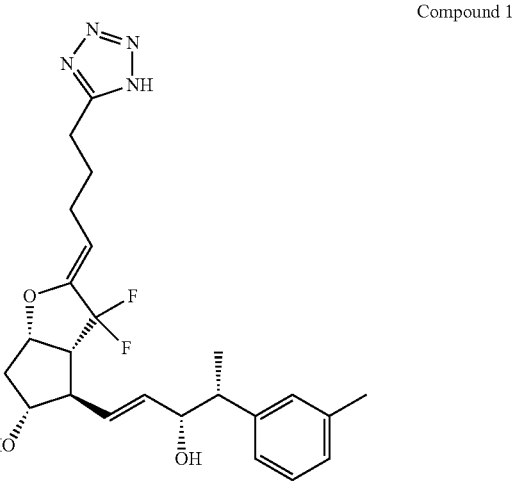

Compound 1

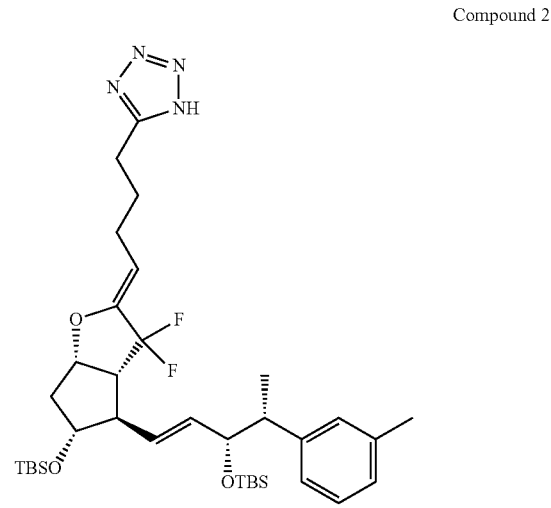

Compound 2

Example 4

To a suspension prepared by mixing 1.5 g (2.2 mmol) of 4-[(Z)-(1S,5R,6R,7R)-6-[(1E,3R,4R)-3-t-butyldimethylsiloxy-4-(m-tolyl)-1-pentenyl]-7-t-butyldimethylsiloxy-2-oxa-4,4-difluoro-bicyclo[3.3.0]octan-3-ylidene]-1-(tetrazol-5-yl)butane (the above compound 2), 27 ml of acetonitrile and 3 ml of water, 0.60 g (4.4 mmol) of sodium hydrogen sulfate monohydrate was added, followed by stirring in air at room temperature. 24 hours later, the liquid was found to be uniform, and after confirming disappearance of the raw materials by thin-layer chromatography, 60 ml of 1.2% sodium bicarbonate water was added, followed by washing three times with 27 ml of heptane. To the acetonitrile-water mixed liquid phase, 1.2 g of sodium hydrogen sulfate was added, followed by extraction with 27 ml of ethyl acetate, and the organic phase was washed with 30 ml of a 5% sodium chloride aqueous solution. The organic phase was concentrated under reduced pressure to obtain 1.1 g of a solid, which was analyzed by NMR, gas chromatography and HPLC, whereby the yield of 4-[(Z)-(1S,5R,6R,7R)-6-[(1E,3R,4R)-3-hydroxy-4-(m-tolyl)-1-pentenyl]-7-hydroxy-2-oxa-4,4-difluoro-bicyclo[3.3.0]octan-3-ylidene]-1-(tetrazol-5-yl)butane (the above compound 1) was 98%.

Examples 5 to 12 and Comparative Examples 1 to 5

The reaction was carried out under the same conditions as in Example 3 except that the type of the acid, the amount of the acid, the solvent, the reaction temperature and the reaction time were respectively changed (Examples 5 to 12). Further, by using an acid other than the acid in the present invention, the reaction was likewise carried out under the same conditions as in Example 3 (Comparative Examples 1 to 5).

The results are shown in Table 1.
In Table 1, abbreviations, etc. are as follows.
$NaHSO_4$: sodium hydrogen sulfate mono-hydrate
TfOH: trifluoromethane sulfonic acid
AN: acetonitrile
THF: tetrahydrofuran
*1: Compound 2 underwent decomposition.
*2: The reaction did not proceed.

water and 5 ml of a saturated sodium chloride aqueous solution were added, followed by extraction twice with 18 ml of ethyl acetate. The organic phase was concentrated under reduced pressure to obtain 0.38 g of a liquid, which was analyzed by gas chromatography and NMR, whereby the yield of 3-phenoxypropane-1,2-diol was 88%.

The structural characteristics of the 3-phenoxypropane-1,2-diol were as follows:
$^1$H-NMR (CDCl$_3$): δ 3.49 (bs, 1H), 3.69-3.83 (3H), 3.96 (d, 2H), 4.07 (m, 1H), 6.87 (m, 2H), 6.94 (m, 1H), 7.24 (m, 2H)

Comparative Example 6

To a solution prepared by adding 0.51 g (1.29 mmol) of bisTBS ether of 3-phenoxypropane-1,2-diol to 10 ml of tetrahydrofuran (THF), 3.8 ml (3.8 mmol) of a 1 mol/L solution of tetrabutylammonium fluoride was added, followed by stirring in a nitrogen atmosphere at room temperature for 3 hours. After confirming disappearance of the raw materials by thin-layer chromatography, 10 ml of saturated sodium bicarbonate water was added, followed by extraction twice with 10 ml of ethyl acetate and then by washing with a saturated sodium chloride aqueous solution. The organic phase was concentrated under reduced pressure to obtain 0.45 g of a liquid, which was analyzed by gas chromatography and NMR, whereby the yield of 3-phenoxypropane-1,2-diol was 89%. In the formed crude product, a tetrabutylammonium salt was contained in an amount of 1.2 times by mol of the 3-phenoxypropane-1,2-diol.

INDUSTRIAL APPLICABILITY

By using the deprotection method of the present invention, it is possible to protect various alcohols by TBS and carry out various reactions, and it is thereby possible to diversify the reaction designs. Particularly, the method of the present invention effectively contributes to designing reactions of alcohols having moieties unstable to acids (e.g. an alcohol having a vinyl ether in its molecule).

TABLE 1

|  | Type of acid | Molar ratio (acid/compound 2) | Solvent | Reaction temperature (° C.) | Reaction time (hr) | Yield of compound 1 (%) |
| --- | --- | --- | --- | --- | --- | --- |
| Ex. 5 | Maleic acid | 1.5 | AN:Water = 3:1 | Room temp. | 28 | >99 |
| Ex. 6 | Maleic acid | 14 | AN:Water = 3:1 | 60 | 2 | 89 |
| Ex. 7 | Oxalic acid | 1.5 | AN:Water = 3:1 | Room temp. | 95 | >99 |
| Ex. 8 | Oxalic acid | 14 | AN:Water = 3:1 | Room temp. | 44 | 95 |
| Ex. 9 | NaHSO$_4$ | 2 | AN:Water = 3:1 | Room temp. | 126 | >99 |
| Ex. 10 | NaHSO$_4$ | 2 | AN:Water = 9:1 | Room temp. | 24 | >99 |
| Ex. 11 | NaHSO$_4$ | 2 | AN:Water = 19:1 | Room temp. | 7 | 98 |
| Ex. 12 | NaHSO$_4$ | 2 | AN:Water = 19:1 | 40 | 8 | 95 |
| Comp. Ex. 1 | Sulfuric acid | 14 | Methanol | Room temp. | 3 | 22*$^1$ |
| Comp. Ex. 2 | TfOH | 14 | THF | 0 | 3 | 0*$^1$ |
| Comp. Ex. 3 | TfOH | 14 | Methylene chloride | Room temp. | 3 | 0*$^1$ |
| Comp. Ex. 4 | Citric acid | 14 | Methanol | Room temp. | 24 | 0*$^2$ |
| Comp. Ex. 5 | Formic acid | 14 | AN:Water = 1:1 | Room temp. | 100 | 0*$^2$ |

Example 13

To a suspension prepared by mixing 1.0 g (2.5 mmol) of bisTBS ether of 3-phenoxypropane-1,2-diol, 18 ml of acetonitrile and 2 ml of water, 0.72 g (5.0 mmol) of sodium hydrogen sulfate monohydrate was added, followed by stirring in air at room temperature for 18 hours. After confirming disappearance of the raw materials by thin-layer chromatography, 18 ml of saturated sodium bicarbonate This application is a continuation of PCT Application No. PCT/JP2012/060623, filed on Apr. 19, 2012, which is based upon and claims the benefit of priority from Japanese Patent Application No. 2011-095211 filed on Apr. 21, 2011. The contents of those applications are incorporated herein by reference in its entirety.

What is claimed is:

1. A method to remove the t-butyldimethylsilyl group from a t-butyldimethylsilyl ether compound of a secondary or tertiary alcohol, comprising:
    preparing a reaction mixture by adding the t-butyldimethylsilyl ether compound and an acid substance to a mixture of water and a solvent selected from the group consisting of a nitrile, an amide and an ester;
    hydrolyzing the t-butyldimethylsilyl ether compound to obtain the secondary or tertiary alcohol; and
    isolating the secondary or tertiary alcohol from the hydrolyzed reaction mixture;
    wherein
    the acid substance is selected from the group consisting of an organic acid, a salt of an organic acid, an inorganic acid and a salt of an inorganic acid; and
    a pKa of the acid substance in water is from 1.0 to 3.0.

2. The method according to claim 1, wherein the isolation comprises:
    adding water or an aqueous sodium chloride solution to the hydrolyzed reaction mixture; and
    extracting the secondary or tertiary alcohol from the aqueous phase with an organic solvent.

3. The method according to claim 1, wherein the acid substance is a carboxylic acid.

4. The method according to claim 3, wherein the carboxylic acid comprises at least two carboxyl groups per molecule.

5. The method according to claim 3, wherein the carboxylic acid is oxalic acid or maleic acid.

6. The method according to claim 1, wherein a proportion of water in the mixed solvent is 0.01≤water/(organic solvent+water)≤0.8 by volume ratio.

7. The method according to claim 1, wherein the hydrolysis reaction temperature is from 0 to 100° C.

8. The method according to claim 1, wherein the secondary or tertiary alcohol comprises at least one moiety unstable to an acid, selected from the group consisting of a vinyl ether moiety, an allyl ether moiety, an allyl alcohol moiety, an acetal moiety, a beta-hydroxycarbonyl moiety, a tetrahydropyranyloxy group, an epoxy group, an amide bond, an ester bond and a polyene moiety.

9. The method of claim 1, wherein the organic solvent is selected from the group consisting of N,N-dimethylformamide, N,N-dimethylacetamide, N-methylpyrrolidone, N,N-dimethylimidazoline, ethyl acetate, acetonitrile and propionitrile.

10. The method of claim 1, wherein the mixture of water and solvent is free of tetrahydrofuran.

11. A method to remove the t-butyldimethylsilyl group from a t-butyldimethylsilyl ether compound of an alcohol, comprising:
    preparing a reaction mixture by adding the t-butyldimethylsilyl ether compound and an acid substance to a mixture of water and a solvent selected from the group consisting of a nitrile, an amide and an ester:
    hydrolyzing the t-butyldimethylsilyl ether compound to obtain the alcohol; and
    isolating the alcohol from the hydrolyzed reaction mixture;
    wherein
    the acid substance is selected from the group consisting of an organic acid, a salt of an organic acid, an inorganic acid and a salt of an inorganic acid:
    a pKa of the acid substance in water is from 1.0 to 3.0,
    the mixture of water and the solvent is free of tetrahydrofuran.

* * * * *